(12) United States Patent
Dusch et al.

(10) Patent No.: US 6,184,007 B1
(45) Date of Patent: Feb. 6, 2001

(54) METHOD FOR THE FERMENTATIVE PRODUCTION OF D-PANTOTHENIC ACID BY ENHANCEMENT OF THE PAND GENE IN MICROORGANISMS

(75) Inventors: Nicole Dusch; Jörn Kalinowski; Alfred Puhler, all of Blelefeld (DE)

(73) Assignee: Degussa-Huls Aktiengesellschaft, Hanau (DE)

( * ) Notice: Under 35 U.S.C. 154(b), the term of this patent shall be extended for 0 days.

(21) Appl. No.: 09/318,793

(22) Filed: May 26, 1999

(30) Foreign Application Priority Data

Dec. 1, 1998 (DE) .............................. 198 55 313

(51) Int. Cl.[7] ................................. C12P 13/00
(52) U.S. Cl. ............ 435/128; 435/252.32; 435/252.33; 435/252.3; 435/254.11; 435/325; 435/419; 435/320.1; 536/23.1; 536/23.2
(58) Field of Search .................. 435/128, 252.33, 435/252.32, 320.1; 536/23.2

(56) References Cited

U.S. PATENT DOCUMENTS 5,518,906 * 5/1996 Hikichi et al. ................. 435/116

FOREIGN PATENT DOCUMENTS 0 493 060 A2 * 7/1992 (EP) ............................ C12P/13/02

OTHER PUBLICATIONS

Weickert et al. Optimization of heterologous protein production in Escherichia coli. Current Opinion in Biotechnology (1996) 7: 494–499.*

Cronan et al. Genetic and Biochemical Analyses of Pantothenate Biosynthesis in Escherichia coli and Salmonella typhimurium. Journal of Bacteriology (1982) 149,3: 916–922.*

Merkel et al. Nucleotide sequence of the Escherichia coli pan BCD gene cluster. (1993) GenBank accession number L17086.*

* cited by examiner

Primary Examiner—Ponnathapu Achutamurthy
(74) Attorney, Agent, or Firm—Pillsbury Madison & Sutro LLP

(57) ABSTRACT

The invention is a method for the production of D-pantothenic acid by the fermentation of microorganisms in which at least the panD gene is enhanced (overexpressed), optionally in combination with the panB and/or panC gene, to provide for the enrichment of the pantothenic acid in the medium or the cells of the microorganisms.

21 Claims, 4 Drawing Sheets

```
                        SEQUENCE LISTING

<160> NUMBER OF SEQ ID NOS:  13

<210> SEQ ID NO 1
<211> LENGTH: 540
<212> TYPE: DNA
<213> ORGANISM: Corynebacterium glutamicum
<220> FEATURE:
<221> NAME/KEY: CDS
<222> LOCATION: (77)..(484)

<400> SEQUENCE: 1
aatattcctt tccttgtcat ctcacgctat gatttctaaa acttgcagga caaccccat        60 aaggacacca caggac atg ctg cgc acc atc ctc gga agt aag att cac cga     112
                Met Leu Arg Thr Ile Leu Gly Ser Lys Ile His Arg
                  1               5                  10 gcc act gtc act caa gct gat cta gat tat gtt ggc tct gta acc atc        160
Ala Thr Val Thr Gln Ala Asp Leu Asp Tyr Val Gly Ser Val Thr Ile
            15                  20                  25 gac gcc gac ctg gtt cac gcc gcc gga ttg atc gaa ggc gaa aaa gtt        208
Asp Ala Asp Leu Val His Ala Ala Gly Leu Ile Glu Gly Glu Lys Val
        30                  35                  40
```

```
gcc atc gta gac atc acc aac ggc gct cgt ctg gaa act tat gtc att    256
Ala Ile Val Asp Ile Thr Asn Gly Ala Arg Leu Glu Thr Tyr Val Ile
 45              50                  55                  60 gtg ggc gac gcc gga acg ggc aat att tgc atc aat ggt gcc gct gca    304
Val Gly Asp Ala Gly Thr Gly Asn Ile Cys Ile Asn Gly Ala Ala Ala
             65                  70                  75 cac ctt att aat cct ggc gat ctt gtg atc atc atg agc tac ctt cag    352
His Leu Ile Asn Pro Gly Asp Leu Val Ile Ile Met Ser Tyr Leu Gln
             80                  85                  90 gca act gat gcg gaa gcc aag gcg tat gag cca aag att gtg cac gtg    400
Ala Thr Asp Ala Glu Ala Lys Ala Tyr Glu Pro Lys Ile Val His Val
         95                 100                 105 gac gcc gac aac cgc atc gtt gcg ctc ggc aac gat ctt gcg gaa gca    448
Asp Ala Asp Asn Arg Ile Val Ala Leu Gly Asn Asp Leu Ala Glu Ala
    110                 115                 120 cta cct gga tcc ggg ctt ttg acg tcg aga agc att tagcgtttta         494
Leu Pro Gly Ser Gly Leu Leu Thr Ser Arg Ser Ile
125                 130                 135 gctcgccaat attgctgccg gcctcgttga aaatggtcat ggtggc                 540

<210> SEQ ID NO 2
<211> LENGTH: 136
<212> TYPE: PRT
<213> ORGANISM: Corynebacterium glutamicum

<400> SEQUENCE: 2

Met Leu Arg Thr Ile Leu Gly Ser Lys Ile His Arg Ala Thr Val Thr
 1               5                  10                  15

Gln Ala Asp Leu Asp Tyr Val Gly Ser Val Thr Ile Asp Ala Asp Leu
             20                  25                  30

Val His Ala Ala Gly Leu Ile Glu Gly Glu Lys Val Ala Ile Val Asp
         35                  40                  45

Ile Thr Asn Gly Ala Arg Leu Glu Thr Tyr Val Ile Val Gly Asp Ala
     50                  55                  60

Gly Thr Gly Asn Ile Cys Ile Asn Gly Ala Ala Ala His Leu Ile Asn
 65                  70                  75                  80

Pro Gly Asp Leu Val Ile Ile Met Ser Tyr Leu Gln Ala Thr Asp Ala
                 85                  90                  95

Glu Ala Lys Ala Tyr Glu Pro Lys Ile Val His Val Asp Ala Asp Asn
            100                 105                 110

Arg Ile Val Ala Leu Gly Asn Asp Leu Ala Glu Ala Leu Pro Gly Ser
        115                 120                 125

Gly Leu Leu Thr Ser Arg Ser Ile
    130                 135

<210> SEQ ID NO 3
<211> LENGTH: 2164
<212> TYPE: DNA
<213> ORGANISM: Corynebacterium glutamicum
<220> FEATURE:
<221> NAME/KEY: CDS
<222> LOCATION: (351)..(1163)
<221> NAME/KEY: CDS
<222> LOCATION: (1166)..(2002)

<400> SEQUENCE: 3
gcttcggggt accaattcct ttaagaacca tcagatcaat ctgttgtaca ttctcggcca    60
gattcagctt ttcggtaagg acgaaacact ttcacttgaa tcggcagcaa agtttcttaa   120
agtttctaag gcaactgcaa cgaggtattt tagaactctc cgagaaatgg aattagttca   180
```

-continued

```
cgaggtcagc aaacgccctt tgcggtttgc gctcacggat aaaggtcgtg agatagtagg        240
tcttgaggta aaaatttgac tccataacga gaacttaatc gagcaacacc cctgaacagt        300
gaatcaaatc ggaatttatt tattctgagc tggtcatcac atctatactc atg ccc           356
                                                         Met Pro
                                                           1
```

| | | | | | | | | | | | | | |
|---|---|---|---|---|---|---|---|---|---|---|---|---|---|
| atg | tca | ggc | att | gat | gca | aag | aaa | atc | cgc | acc | cgt | cat | ttc cgc gaa | 404 |
| Met | Ser | Gly | Ile | Asp | Ala | Lys | Lys | Ile | Arg | Thr | Arg | His | Phe Arg Glu |
| | | 5 | | | | 10 | | | | 15 | | | |

```
gct aaa gta aac ggc cag aaa gtt tcg gtt ctc acc agc tat gat gcg         452
Ala Lys Val Asn Gly Gln Lys Val Ser Val Leu Thr Ser Tyr Asp Ala
     20              25                  30 ctt tcg gcg cgc att ttt gat gag gct ggc gtc gat atg ctc ctt gtt         500
Leu Ser Ala Arg Ile Phe Asp Glu Ala Gly Val Asp Met Leu Leu Val
 35              40                  45                  50 ggt gat tcc gct gcc aac gtt gtg ctg ggt cgc gat acc acc ttg tcg         548
Gly Asp Ser Ala Ala Asn Val Val Leu Gly Arg Asp Thr Thr Leu Ser
                 55                  60                  65 atc acc ttg gat gag atg att gtg ctg gcc aag gcg gtg acg atc gct         596
Ile Thr Leu Asp Glu Met Ile Val Leu Ala Lys Ala Val Thr Ile Ala
             70                  75                  80 acg aag cgt gcg ctt gtg gtg gtt gat ctg ccg ttt ggt acc tat gag         644
Thr Lys Arg Ala Leu Val Val Val Asp Leu Pro Phe Gly Thr Tyr Glu
         85                  90                  95 gtg agc cca aat cag gcg gtg gag tcc gcg atc cgg gtc atg cgt gaa         692
Val Ser Pro Asn Gln Ala Val Glu Ser Ala Ile Arg Val Met Arg Glu
    100                 105                 110 acg ggt gcg gct gcg gtg aag atc gag ggt ggc gtg gag atc gcg cag         740
Thr Gly Ala Ala Ala Val Lys Ile Glu Gly Gly Val Glu Ile Ala Gln
115                 120                 125                 130 acg att cga cgc att gtt gat gct gga att ccg gtt gtc ggc cac atc         788
Thr Ile Arg Arg Ile Val Asp Ala Gly Ile Pro Val Val Gly His Ile
                135                 140                 145 ggg tac acc ccg cag tcc gag cat tcc ttg ggc ggc cac gtg gtt cag         836
Gly Tyr Thr Pro Gln Ser Glu His Ser Leu Gly Gly His Val Val Gln
            150                 155                 160 ggt cgt ggc gcg agt tct gga aag ctc atc gcc gat gcc cgc gcg ttg         884
Gly Arg Gly Ala Ser Ser Gly Lys Leu Ile Ala Asp Ala Arg Ala Leu
        165                 170                 175 gag cag gcg ggt gcg ttt gcg gtt gtg ttg gag atg gtt cca gca gag         932
Glu Gln Ala Gly Ala Phe Ala Val Val Leu Glu Met Val Pro Ala Glu
    180                 185                 190 gca gcg cgc gag gtt acc gag gat ctt tcc atc acc act atc gga atc         980
Ala Ala Arg Glu Val Thr Glu Asp Leu Ser Ile Thr Thr Ile Gly Ile
195                 200                 205                 210 ggt gcc ggc aat ggc aca gat ggg cag gtt ttg gtg tgg cag gat gcc        1028
Gly Ala Gly Asn Gly Thr Asp Gly Gln Val Leu Val Trp Gln Asp Ala
                215                 220                 225 ttc ggc ctc aac cgc ggc aag aag cca cgc ttc gtc cgc gag tac gcc        1076
Phe Gly Leu Asn Arg Gly Lys Lys Pro Arg Phe Val Arg Glu Tyr Ala
            230                 235                 240 acc ttg ggc gat tcc ttg cac gac gcc gcg cag gcc tac atc gcc gat        1124
Thr Leu Gly Asp Ser Leu His Asp Ala Ala Gln Ala Tyr Ile Ala Asp
        245                 250                 255 atc cac gcg ggt acc ttc cca ggc gaa gcg gag tcc ttt ta atg cag         1171
Ile His Ala Gly Thr Phe Pro Gly Glu Ala Glu Ser Phe     Met Gln
    260                 265                 270 gta gca acc aca aag cag gcg ctt atc gac gcc ctc ctc cac cac aaa        1219
Val Ala Thr Thr Lys Gln Ala Leu Ile Asp Ala Leu Leu His His Lys
```

-continued

|  |  |  |  |  |  |  |  |  |  |  |  |  |  |  |  |
|---|---|---|---|---|---|---|---|---|---|---|---|---|---|---|---|
|  | 275 |  |  |  | 280 |  |  |  | 285 |  |  |  |  |  |  |

```
tcc gtc ggg ctc gtc ccc acc atg ggt gcg cta cac agc gga cac gcc    1267
Ser Val Gly Leu Val Pro Thr Met Gly Ala Leu His Ser Gly His Ala
290                 295                 300                 305 tcg ttg gtt aaa gca gca cgc gct gaa aac gac act gtt gta gcc agt    1315
Ser Leu Val Lys Ala Ala Arg Ala Glu Asn Asp Thr Val Val Ala Ser
                310                 315                 320 att ttt gtc aat ccc ctg cag ttt gaa gca ctc ggt gat tgc gat gat    1363
Ile Phe Val Asn Pro Leu Gln Phe Glu Ala Leu Gly Asp Cys Asp Asp
            325                 330                 335 tac cgc aac tat ccc cgc caa ctc gac gcc gat tta gca ctg ctt gaa    1411
Tyr Arg Asn Tyr Pro Arg Gln Leu Asp Ala Asp Leu Ala Leu Leu Glu
        340                 345                 350 gag gca ggt gtg gat att gtg ttc gca ccc gat gtg gag gaa atg tac    1459
Glu Ala Gly Val Asp Ile Val Phe Ala Pro Asp Val Glu Glu Met Tyr
    355                 360                 365 ccc ggt ggc ttg cca cta gtg tgg gcg cgc acc ggt tcc atc gga aca    1507
Pro Gly Gly Leu Pro Leu Val Trp Ala Arg Thr Gly Ser Ile Gly Thr
370                 375                 380                 385 aaa ttg gag ggt gcc agc agg cct ggc cat ttc gat ggt gtg gct acc    1555
Lys Leu Glu Gly Ala Ser Arg Pro Gly His Phe Asp Gly Val Ala Thr
                390                 395                 400 gtg gtg gcg aag ctg ttc aat ttg gtg cgc cct gat cgt gca tat ttt    1603
Val Val Ala Lys Leu Phe Asn Leu Val Arg Pro Asp Arg Ala Tyr Phe
            405                 410                 415 gga caa aaa gat gct cag cag gtt gcg gtg att cgg cga ttg gtt gcc    1651
Gly Gln Lys Asp Ala Gln Gln Val Ala Val Ile Arg Arg Leu Val Ala
        420                 425                 430 gat cta gac att ccc gtg gag att cgt ccc gtt ccg att att cgt ggc    1699
Asp Leu Asp Ile Pro Val Glu Ile Arg Pro Val Pro Ile Ile Arg Gly
    435                 440                 445 gcc gat ggc tta gcc gaa tcc agc cgc aat caa cgt ctt tct gcg gat    1747
Ala Asp Gly Leu Ala Glu Ser Ser Arg Asn Gln Arg Leu Ser Ala Asp
450                 455                 460                 465 cag cga gcg caa gct ctg gtg ctg ccg cag gtg ttg agt ggg ttg cag    1795
Gln Arg Ala Gln Ala Leu Val Leu Pro Gln Val Leu Ser Gly Leu Gln
                470                 475                 480 cgt cga aaa gca gct ggt gaa gcg cta gat atc caa ggt gcg cgc gac    1843
Arg Arg Lys Ala Ala Gly Glu Ala Leu Asp Ile Gln Gly Ala Arg Asp
            485                 490                 495 acc ttg gcc agc gcc gac ggc gtg cgc ttg gat cac ctg gaa att gtc    1891
Thr Leu Ala Ser Ala Asp Gly Val Arg Leu Asp His Leu Glu Ile Val
        500                 505                 510 gat cca gcc acc ctc gaa cca tta gaa atc gac ggc ctg ctc acc caa    1939
Asp Pro Ala Thr Leu Glu Pro Leu Glu Ile Asp Gly Leu Leu Thr Gln
    515                 520                 525 cca gcg ttg gtg gtc ggc gcg att ttc gtg ggg ccg gtg cgg ttg atc    1987
Pro Ala Leu Val Val Gly Ala Ile Phe Val Gly Pro Val Arg Leu Ile
530                 535                 540                 545 gac aat atc gag ctc tagtaccaac cctgcgttgc agcacgcagc ttcgcataac    2042
Asp Asn Ile Glu Leu
                550 gcgtgctcag ctcagtgttt ttaggtgcgc ggtgcggatc ggaaccggga gttggccact    2102 gcggtggcgt ggcctcaccc gacagcgccc atgccgcctg acgagctgca cccaacgcca    2162 ca                                                                  2164
```

<210> SEQ ID NO 4
<211> LENGTH: 271

-continued

```
<212> TYPE: PRT
<213> ORGANISM: Corynebacterium glutamicum

<400> SEQUENCE: 4

Met Pro Met Ser Gly Ile Asp Ala Lys Lys Ile Arg Thr Arg His Phe
 1               5                  10                  15

Arg Glu Ala Lys Val Asn Gly Gln Lys Val Ser Val Leu Thr Ser Tyr
             20                  25                  30

Asp Ala Leu Ser Ala Arg Ile Phe Asp Glu Ala Gly Val Asp Met Leu
         35                  40                  45

Leu Val Gly Asp Ser Ala Ala Asn Val Val Leu Gly Arg Asp Thr Thr
     50                  55                  60

Leu Ser Ile Thr Leu Asp Glu Met Ile Val Leu Ala Lys Ala Val Thr
 65                  70                  75                  80

Ile Ala Thr Lys Arg Ala Leu Val Val Asp Leu Pro Phe Gly Thr
                 85                  90                  95

Tyr Glu Val Ser Pro Asn Gln Ala Val Glu Ser Ala Ile Arg Val Met
            100                 105                 110

Arg Glu Thr Gly Ala Ala Val Lys Ile Glu Gly Gly Val Glu Ile
        115                 120                 125

Ala Gln Thr Ile Arg Arg Ile Val Asp Ala Gly Ile Pro Val Val Gly
    130                 135                 140

His Ile Gly Tyr Thr Pro Gln Ser Glu His Ser Leu Gly Gly His Val
145                 150                 155                 160

Val Gln Gly Arg Gly Ala Ser Ser Gly Lys Leu Ile Ala Asp Ala Arg
                165                 170                 175

Ala Leu Glu Gln Ala Gly Ala Phe Ala Val Val Leu Glu Met Val Pro
            180                 185                 190

Ala Glu Ala Ala Arg Glu Val Thr Glu Asp Leu Ser Ile Thr Thr Ile
        195                 200                 205

Gly Ile Gly Ala Gly Asn Gly Thr Asp Gly Gln Val Leu Val Trp Gln
    210                 215                 220

Asp Ala Phe Gly Leu Asn Arg Gly Lys Lys Pro Arg Phe Val Arg Glu
225                 230                 235                 240

Tyr Ala Thr Leu Gly Asp Ser Leu His Asp Ala Ala Gln Ala Tyr Ile
                245                 250                 255

Ala Asp Ile His Ala Gly Thr Phe Pro Gly Glu Ala Glu Ser Phe
            260                 265                 270

<210> SEQ ID NO 5
<211> LENGTH: 279
<212> TYPE: PRT
<213> ORGANISM: Corynebacterium glutamicum

<400> SEQUENCE: 5

Met Gln Val Ala Thr Thr Lys Gln Ala Leu Ile Asp Ala Leu Leu His
 1               5                  10                  15

His Lys Ser Val Gly Leu Val Pro Thr Met Gly Ala Leu His Ser Gly
             20                  25                  30

His Ala Ser Leu Val Lys Ala Ala Arg Ala Glu Asn Asp Thr Val Val
         35                  40                  45

Ala Ser Ile Phe Val Asn Pro Leu Gln Phe Glu Ala Leu Gly Asp Cys
     50                  55                  60

Asp Asp Tyr Arg Asn Tyr Pro Arg Gln Leu Asp Ala Asp Leu Ala Leu
 65                  70                  75                  80
```

```
Leu Glu Glu Ala Gly Val Asp Ile Val Phe Ala Pro Asp Val Glu Glu
                 85                  90                  95

Met Tyr Pro Gly Gly Leu Pro Leu Val Trp Ala Arg Thr Gly Ser Ile
            100                 105                 110

Gly Thr Lys Leu Glu Gly Ala Ser Arg Pro Gly His Phe Asp Gly Val
        115                 120                 125

Ala Thr Val Val Ala Lys Leu Phe Asn Leu Val Arg Pro Asp Arg Ala
    130                 135                 140

Tyr Phe Gly Gln Lys Asp Ala Gln Gln Val Ala Val Ile Arg Arg Leu
145                 150                 155                 160

Val Ala Asp Leu Asp Ile Pro Val Glu Ile Arg Pro Val Pro Ile Ile
                165                 170                 175

Arg Gly Ala Asp Gly Leu Ala Glu Ser Ser Arg Asn Gln Arg Leu Ser
            180                 185                 190

Ala Asp Gln Arg Ala Gln Ala Leu Val Leu Pro Gln Val Leu Ser Gly
        195                 200                 205

Leu Gln Arg Arg Lys Ala Ala Gly Glu Ala Leu Asp Ile Gln Gly Ala
    210                 215                 220

Arg Asp Thr Leu Ala Ser Ala Asp Gly Val Arg Leu Asp His Leu Glu
225                 230                 235                 240

Ile Val Asp Pro Ala Thr Leu Glu Pro Leu Glu Ile Asp Gly Leu Leu
                245                 250                 255

Thr Gln Pro Ala Leu Val Val Gly Ala Ile Phe Val Gly Pro Val Arg
            260                 265                 270

Leu Ile Asp Asn Ile Glu Leu
        275

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 6
gaattcgaca gggtagaaag gtaga                                         25

<210> SEQ ID NO 7
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 7
agatctggga taacaatcaa gcaacc                                        26

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Primer

<400> SEQUENCE: 8
catctcacgc tatgaattct                                               20

<210> SEQ ID NO 9
<211> LENGTH: 18
<212> TYPE: DNA
```

```
<213> ORGANISM: Artificial Sequence
<220> FEATURE:
<223> OTHER INFORMATION: Description of Artificial Sequence: Primer

<400> SEQUENCE: 9
acgaggcctg cagcaata                                                    18

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 10
ggatcccaca acatcaattt atcagg                                           26

<210> SEQ ID NO 11
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 11
ggatccttaa gtattacgcc agctc                                            25

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 12
gtcgactctg agctggtcat cacatc                                           26

<210> SEQ ID NO 13
<211> LENGTH: 26
<212> TYPE: DNA
<213> ORGANISM: Artificial Sequence
<220> FEATURE:
<223> OTHER INFORMATION: Description of Artificial Sequence: Primer

<400> SEQUENCE: 13
gtcgacacgc agggttggta ctagag                                           26
```

METHOD FOR THE FERMENTATIVE PRODUCTION OF D-PANTOTHENIC ACID BY ENHANCEMENT OF THE PAND GENE IN MICROORGANISMS

BACKGROUND OF THE INVENTION

Pantothenic acid is a commercially significant vitamin which is used in cosmetics, medicine, human nourishment and in animal nourishment.

Pantothenic acid can be produced by chemical synthesis or biotechnologically by the fermentation of suitable microorganisms in suitable nutrient solutions. DL-pantolactone is an important intermediate stage in the chemical synthesis. It is produced in a multi-stage process from formaldehyde, isobutylaldehyde and cyanide. In further method steps the racemic mixture is separated and D-pantolactone condensed with β-alanine and D-pantothenic acid obtained. The advantage of the fermentative production with microorganisms resides in the direct formation of the desired stereoisomeric D-form, which is free of L-pantothenic acid.

Various types of bacteria such as, for example, *Escherichia coli, Arthrobacter ureafaciens, Corynebacterium erythrogenes, Brevibacterium ammoniagenes* and also yeasts such as, for example, *Debaromyces castellii* can produce D-pantothenic acid in a nutrient solution containing glucose, DL-pantoic acid and β-alanine, as is shown in EP-A 0,493,060. EP-A 0,493,060 also shows that the formation of D-pantothenic acid is improved in the case of *Escherichia coli* by amplification of pantothenic-acid biosynthetic genes from *E. coli*, which are contained on the plasmids pFV3 and pFV5, in a nutrient solution containing glucose, DL-pantoic acid and β-alanine.

EP-A 0,590,857 and U.S. Pat. No. 5,518,906 describe mutants derived from *Escherichia coli* strain IFO3547 such as FV5714, FV525, FV814, FV521, FV221, FV6051 and FV5069 which carry resistance genes against various antimetabolites such as salicylic acid, α-ketobutyric acid, β-hydroxyaspartic acid, O-methylthreonine and α-ketoisovaleric acid and produce D-pantothenic acid in a nutrient solution containing glucose, pantoic acid and in a nutrient solution containing glucose and β-alanine. E-A 0,590,857 and U.S. Pat. No. 5,518,906 also show that after the amplification of the pantothenic-acid biosynthesis genes contained on the plasmid pFV31, in the strains cited above, the production of D-pantoic acid is improved in a nutrient solution containing glucose and that the production of D-pantothenic acid is improved in a nutrient solution containing glucose and β-alanine.

Moreover, WO97/10340 shows that the production of pantothenic acid can be further increased in strains of *Escherichia coli* forming pantothenic acid by elevating the activity of the enzyme acetohydroxy-acid synthase II, an enzyme of valine biosynthesis.

SUMMARY OF THE INVENTION

It is an object of the invention to provide novel bases for improved methods for the fermentative production of pantothenic acid.

Pantothenic acid, or Vitamin B3, is a commercially significant product which is used in cosmetics, medicine, human nourishment and in animal nourishment. There is therefore general interest in making available novel methods of producing pantothenic acid.

When D-pantothenic acid or pantothenic acid or pantothenate are mentioned in the following text not only the free acid but also the salts of D-pantothenic acid such as, for example, the calcium salt, sodium salt, ammonium salt or potassium salt are meant.

Subject matter of the invention includes, among other things, a method for the fermentative production of D-pantothenic acid using microorganisms which, in particular, already produce D-pantothenic acid and in which the panD gene coding for L-aspartate-1-decarboxylase (E.C. 4.1.1.11) is enhanced, especially overexpressed individually or in combination with the genes panB and/or panC. The invention relates to corresponding recombinant DNA sequences like those documented in the claims. The invention also includes methods for the fermentative production of D-pantothenic acid which are carried out using the improved microorganisms produced according to the invention which produce D-pantothenic acid.

The concept "enhancement" describes in this connection the elevation of the intracellular activity of one or several enzymes in a microorganism which are coded by the corresponding DNA in that, for example, the copy number of the gene(s) is increased, a strong promoter is used or a gene is used which codes for a corresponding enzyme with a high activity and optionally combines these measures.

The microorganisms constituting the subject matter of the present invention can produce pantothenic acid from glucose, saccharose, lactose, fructose, maltose, molasses, starch, cellulose or from glycerol and ethanol. They can be fungi or yeasts or Gram-positive bacteria, for example, of the genus Corynebacterium, or Gram-negative bacteria such as, for example, those of the Enterobacteriaceae. In the family of Enterobacteriaceae the genus Escherichlia with the species *Escherichia coli* is to be cited in particular. Within the species *Escherichia coli* the so-called K-12 strains such as, for example, the strains MG1655 or W3110 (Neidhard et al.: *Escherichia coli* and Salmonella. Cellular and Molecular Biology (ASM Press, Washington, D.C.)) or the *Escherichia coli* wild-type strain IFO03547 (Institute for Fermentation, Osaka, Japan) and mutants derived from them are to be cited. In the genus Corynebacterium especially the species *Corynebacterium glutamicum* is to be cited, which is known to the skilled artisan for its ability to produce amino acids. This species includes wild-type strains such as, for example, *Corynebacterium glutamicum* ATCC13032, *Brevibacterium flavum* ATCC14067, *Corynebacterium melassecola* ATCC17965 and mutants derived from them.

The present inventors discovered that microorganisms produce pantothenic acid in an improved manner after overexpression of the novel panD gene, especially from *Corynebacterium glutamicum*, coding for L-aspartate-1-decarboxylase (E.C. 4.1.1.11).

The inventors discovered in addition that the overexpression of the panD gene has an advantageous effect in strains in which the genes panB and panC coding for ketopantoate hydroxymethyltransferase and pantothenate synthetase are additionally present in an overexpressed state either individually or together.

In order to achieve an overexpression, the copy number of the corresponding genes can be elevated or the promoter and regulatory region, which is located upstream from the structural gene, can be mutated. Expression cassettes which are inserted upstream from the structural gene operate in the same manner. It is additionally possible to increase the expression in the course of the fermentative formation of D-pantothenate by inducible promoters. The expression is likewise improved by measures for extending the life of m-RNA. Furthermore, the enzymatic activity is likewise enhanced by preventing the degradation of the enzymatic protein. The genes or gene constructs can be present either in plasmids with different copy number or be integrated in the chromosome and amplified. Alternatively, an overexpression of the genes concerned can furthermore be achieved by altering the composition of the media and conduction of the culture.

An expert in the art will find instructions for this in, among others, Martin et al. (Bio/Technology 5, 137–146 (1987)), in Guerrero et al. (Gene 138, 35–41 (1994)), Tsuchiya and Morinaga (Bio/Technology 6, 428–430 (1988)), in Eikmanns et al. (Gene 102, 93–98 (1991)), in European patent EPS 0,472,869, in U.S. Pat. No. 4,601,893, in Schwarzer and Pühler (Bio/Technology 9, 84–87 (1991), in Reinscheid et al., (Applied and Environmental Microbiology 60, 126–132 (1994)), in LaBarre et al. (Journal of Bacteriology 175, 1001–1007 (1993)), in patent application WO 96/15246, in Jensen and Hammer (Biotechnology and Bioengineering 58, 191–195 (1998)) or in the manual "Manual of Methods for general Bacteriology of the American Society for Bacteriology (Washington, D.C., USA, 1981). In addition, an expert in the art will find instructions in Chang and Cohen (Journal of Bacteriology 134: 1141–1156 (1978)), in Hartley and Gregori (Gene 13: 347–353 (1981)), in Amann and Brosius (Gene 40: 183–190 (1985)), in de Broer et al., (Proceedings of the National Academy of Sciences of the United States of America 80: 21–25(1983)), in LaVallie et al. (BIO/TECHNOLOGY 11, 187–193 (1993)), in PCT/US97/13359in Llosa et al. (Plasmid 26: 222–224 (1991)), in Quandt and Klipp (Gene 80: 161–169 (1989)), in Hamilton (Journal of Bacteriology 171: 4617–4622 (1989)), in Makrides (Microbiological Reviews 60:512–538 (1996)) and in known textbooks of genetics and molecular biology.

In order to isolate the panD gene or other genes such as, for example, the genes panB and panC from *C. glutamicum*, at first a gene bank of this microorganism is established in *E. coli*. The establishment of gene banks is documented in generally known textbooks and manuals. The textbook of Winnacker: Gene und Klone, Eine Einführung in die Gentechnologie [German—Genes and Clones, An Introduction to Gene Technology] (Verlag Chemie, Weinheim, Germany, 1990) or the manual of Sambrook et al.: Molecular Cloning, A Laboratory Manual (Cold Spring Harbor Laboratory Press, 1989) are cited as examples. A known gene bank is that of the *E. coli* K-12 strain W3110 established by Kohara et al. (Cell 50, 495–508 (1987)) in λ vectors. Bathe et al. (Molecular and General Genetics, 252:255–265, 1996) describe a gene bank of *C. glutamicum* ATCC13032 which was established with the aid of the cosmid vector SuperCos I (Wahl et al., 1987, Proceedings of the National Academy of Sciences USA, 84:2160–2164) in the *E. coli* strain K-12 NM554 (Raleigh et al., 1988, Nucleic Acids Research 16:1563–1575). In order to produce a gene bank of *C. glutamicum* in *E. coli*, even plasmids such as pBR322 (Bolivar, Life Sciences, 25, 807–818 (1979)) or pUC9 (Vieira et al., 1982, Gene 25: 259–268) can be used. Suitable hosts are especially those *E. coli* strains which are restriction-defective and recombination-defective. An example for this is the strain DH5αmcr described by Grant et al., (Proceedings of the National Academy of Sciences USA, 87 (1990) 4645–4649).

The gene bank is subsequently inserted into an indicator strain by transformation (Hanahan, Journal of Molecular Biology 166, 557–580, 1983) or electroporation (Tauch et al., 1994, FEMS Microbiological Letters, 123:343–347). The indicator strain is distinguished in that it comprises a mutation in the gene constituting the object of interest which causes a detectable phenotype, for example, an auxotrophy. In the framework of the present invention the *E. coli* mutant DV9 (Vallari and Rock, Journal of Bacteriology 1985, 164:136–142), which carries a mutation in the panD gene, is especially interesting. Another example of an *E. coli* mutant needing pantothenic acid is the strain SJ2, which carries a mutation in the panB gene and can be ordered from the Genetic Stock Center of Yale University (New Haven, Conn., USA). After transformation of the indicator strain such as, for example, the panD mutant DV9 with a recombinant plasmid which carries the gene constituting the object of interest such as, for example, the panD gene and expression of the gene concerned, the indicator strain becomes prototrophic as regards the corresponding property such as, for example, the need for pantothenic acid. The gene or DNA fragment isolated in this manner can be characterized by determination of the sequence as described, for example, in Sanger et al. (Proceedings of the National Academy of Sciences of the United States of America USA, 74:5463–5467, 1977). Subsequently, the degree of identity with known genes contained in data banks such as, for example, the GenBank (Benson et al., 1998, Nucleic Acids Research, 26:1–7) can be analyzed with published methods (Altschul et al., 1990, Journal of Molecular Biology 215:403–410).

In this manner the novel DNA sequence of *C. glutamicum* coding for the gene panD was obtained, which is a component of the present invention as SEQ ID NO:1. Furthermore, the amino-acid sequences of the corresponding enzymes were derived from the present DNA sequence with the methods described above. The resulting amino-acid sequence of the panD gene product, namely, L-aspartate 1-decarboxylase, is shown in SEQ ID NO:2. Furthermore, the novel DNA sequence of *C. glutamicum* coding for the genes panB and panC was obtained in this manner, which DNA sequence is a component of the present invention as SEQ ID NO:3. The resulting amino-acid sequence of the panB gene product, namely, ketopantoate hydroxymethyltransferase, is shown in SEQ ID NO:4 and in SEQ ID NO:5 the resulting amino-acid sequence of the panC gene product, namely, pantothenate synthetase.

Coding DNA sequences resulting from SEQ ID NO:1 and/or SEQ ID NO:3 through the degeneracy of the genetic code are likewise components of the invention. In the same manner DNA sequences which hybridize with SEQ ID NO:1 and/or SEQ ID NO:3 are components of the invention. Furthermore, in the technical world conservative amino-acid exchanges such as, for example, the exchange of glycine for alanine or of aspartic acid for glutamic acid in proteins are known as sense mutations which do not result in any basic change of the activity of the protein, that is, they are functionally neutral. It is furthermore known that changes on the N- and/or C terminus of a protein do not significantly affect its function in an adverse manner or can even stabilize it. An expert in the art will find data about this in, among other locations, Ben-Bassat et al., (Journal of Bacteriology 169:751–757 (1987)), in O'Regan et al., (Gene 77:237–251 (1989)), in Sahin-Toth et al., (Protein Sciences 3:240–247 (1994)), in Hochuli et al., (Bio/Technology 6:1321–1325 (1988)) and in known textbooks of genetics and molecular biology. Amino-acid sequences resulting in a corresponding manner from SEQ ID NO:2, SEQ ID NO:4 and/or SEQ ID NO:5 are likewise components of the invention.

The gene isolated and characterized in this manner can be subsequently brought to expression individually or in combination with others in a suitable microorganism. A known method for expressing or overexpressing genes consists in amplifying them with the aid of plasmid vectors which can be provided in addition with expression signals. Those plasmid vectors which can replicate in the corresponding microorganisms can be considered as plasmid vectors. For *Escherichia coli*, for example, the vectors pSC101 (Vocke and Bastia, Proceedings of the National Academy of Sciences USA 80 (21), 6557–6561 (1983)) or pKK223-3 (Brosius and Holy, Proceedings of the National Academy of Sciences USA 81, 6929 (1984)), for *Corynebacterium glutamicum*, for example, the vector pEKEx1 (Eikmanns et al., Gene 102:93–98 (1991)) or pZ8-1 (European patent 0,375,889) can be considered for the present invention. Examples of such microorganisms are the *C. glutamicum* strains ATCC13032/pND-D2 and ATCC13032/pND-DBC2 and the *E. coli* strain MG1655/pND-D2, which contain the plasmids pND-D2 and pND-DBC2. Plasmid pND-D2 is an *E. coli-C. glutamicum* shuttle vector which is based on the plasmid pZ8-1 and carries the panD gene of *C. glutamicum*. Plasmid pND-DBC2 is an *E. coli-C. glutamicum* shuttle vector which is based on the plasmid pZ8-1 and carries the panD, panB and panC genes of *C. glutamicum*.

It is obvious to an expert in the art that chromosomal mutations which bring about resistances against metabolites and antimetabolites or which prevent the reduction of precursors of pantothenic acid can be combined in an advantageous manner with the measures constituting subject matter of the invention.

The microorganisms produced in accordance with the invention can be cultivated continuously or discontinuously in a batch method (batch cultivation) or in a feed batch method or repeated feed batch method for the purpose of producing pantothenic acid. A summary of known cultivation methods is described in the textbook by Chmiel (Bioprocesstechnik 1. Einführung in die Bioverfahrenstechnik [German-Bioprocessing Technology 1. Introduction to Bioengineering Technologyl ] (Gustav Fischer Verlag, Stuttgart, 1991)) or in the textbook of Storhas (Bioreaktoren and periphere Einrichtungen [German-Bioreactors and Peripheral Apparatuses ] (Vieweg Verlag, Braunschweig/ Wiesbaden, 1994)).

The culture medium to be used must satisfy the demands of the particular microorganisms. Descriptions of culture media of various microorganisms are contained in the manual "Manual of Methods for general Bacteriology" of the American Society for Bacteriology (Washington, DC, USA, 1981). Sugars and carbohydrates such as, for example, glucose, saccharose, lactose, fructose, maltose, molasses, starch and cellulose, oils and fats such as, for example, soy oil, sunflower oil, peanut oil and coconut fat, fatty acids such as, for example, palmitic acid, stearic acid and lineic acid, alcohols such as, for example, glycerol and ethanol and organic acids such as, for example, acetic acid can be used as carbon source. These substances can be used individually or as a mixture. Organic, nitrogen-containing compounds such as peptones, yeast extract, meat extract, malt extract, corn steep liquor, soybean meal and urea or inorganic compounds such as ammonium sulfate, ammonium chloride, ammonium phosphate, ammonium carbonate and ammonium nitrate can be used as nitrogen source. The nitrogen sources can be used individually or as a mixture. Potassium dihydrogenphosphate or dipotassium hydrogenphosphate or the corresponding sodium-containing salts can be used as phosphorus source. The culture medium must also contain metal salts such as, for example, magnesium sulfate or iron sulfate, which are necessary for growth. Finally, essential growth substances such as amino acids and vitamins can be used in addition to the substances cited above. Moreover, precursors of pantothenic acid such as aspartate, β-alanine, ketoisovalerate, ketopantoic acid or pantoic acid and optionally their salts can be added to the culture medium for an additional increase in the production of pantothenic acid. The cited substances to be used can be added to the culture in the form of a one-time batch or supplied in a suitable manner during the cultivation.

Basic compounds such as sodium hydroxide, potassium hydroxide, ammonia or acidic compounds such as phosphoric acid or sulfuric acid are added in a suitable manner for controlling the pH of the culture. Anti-foaming agents such as, for example, fatty-acid polyglycolester can be added for controlling the development of foam. In order to maintain the stability of plasmids, suitable, selectively acting substances, for example, antibiotics can be added to the medium. In order to maintain aerobic conditions, oxygen or oxygen-containing gas mixtures such as, for example, air are charged into the culture. The temperature of the culture is normally approximately 20° C. to 50° C. and preferably approximately 25° C. to 45° C. The culture is continued until a maximum of pantothenic acid has formed. This goal is normally achieved within 10 hours to 160 hours.

Strains with a high activity of the enzyme L-aspartate 1-decarboxylase can also be used for the production of β-alanine from L-aspartate. Fermentative methods, enzymatic conversion reactions or combinations of both can be used for this.

The concentration of pantothenic acid formed can be determined with known methods (Velisek; Chromatographic Science 60, 515–560 (1992)).

The following microorganisms were deposited on Oct. 5, 1998 with the German Collection for Microorganisms and Cell Cultures (DSMZ, Mascheroder Weg 1b, D38124 Braunschweig, Germany) in accordance with the Budapest Convention:

Corynebacterium glutamicum ATCC13032/pND-D2 as DSM12438

Corynebacterium glutamicum ATCC13032/pND-DBC2 as DSM12437.

DETAILED DESCRIPTION OF THE INVENTION

The present invention is explained in detail in the following using exemplary embodiments.

EXAMPLE 1

Cloning and sequencing of the panD gene of *C. glutamicum*

1. Cloning of the panD gene

Chromosomal DNA from *C. glutamicum* ATCC13032 was isolated as described in Tauch et al. (1995, Plasmid, 33:168–179) and partially cleaved with the restriction enzyme Sau3A (Pharmacia Biotech (Freiburg, Germany), product description Sau3A, code No. 27-0913-02). DNA fragments in a size range of 7–9 kb were isolated with the aid of the "Nucleotrap Extraction Kit for Nucleic Acids" (Macherey and Nagel, Düren, Germany; cat. No. 740584) and ligated into the dephosphorylated BamHI cleavage site of vector pUC19 (Norrander et al., 1982, Gene, 26:101–1–6), which was ordered from the company MBI Fermentas (Vilnius, Lithuania). The ligation was carried out as by Sambrook et al. (1989, Molecular Cloning: A Laboratory Manual, Cold Spring Harbor), during which the DNA mixture was incubated overnight with T4 ligase (Pharmacia Biotech, Freiburg, Germany). This ligation mixture was subsequently electroporated into the *E. coli* strain DH5αMCR (Grant, 1990, (Proceedings of the National Academy of Sciences USA, 87:4645–4649) (Tauch, 1994, FEMS Microbiological Letters, 123:343–347) and plated out onto LB agar (Lennox, 1955, Virology, 1:190)+100 μg/ml ampicillin. After incubation for 24 hours at 37° C. the *C. glutamicum* gene bank was able to be obtained from the transformants by re-isolation of the plasmid DNA according to the "alkaline lysis method" of Birnboim and Doly (Nucleic Acids Research, 7:1513–1523, 1997). Competent cells of the *E. coli* strain DV9 (Vallari and Rock, 1985, Journal of Bacteriology, 164:136–142), which carries a mutation in the panD gene, were electroporated with this gene bank. The electroporation batch was washed twice following the regeneration phase (Tauch et al., 1994, FEMS Microbiological Letters, 123: 343–347) with medium E (Vogel and Bonner, 1956, Journal of Biological Chemistry, 218:97–106). The composition of medium E is shown in Table 1. 50 ml medium E+100 μg/ml ampicillin, which were in a 250 ml Erlenmeyer flask, were inoculated with these cells and incubated in an air agitator at 250 U/min and 19° C. After a two-day incubation the bacterial suspension was diluted and spread out onto LB agar (Lennox, 1955, Virology, 1:190) which had been supplemented with 100 μg/ml ampicillin.

TABLE 1

| Substance | Amount per liter | Comments |
| --- | --- | --- |
| $K_2HPO_4$ | 10 g | |
| $NaNH_4HPO_4 * 4 H_2O$ | 3.5 g | |
| citric acid | 2 g | |
| $MgSO_4 * 7 H_2O$ | 0.2 g | |
| glucose | 4 g | sterilize separately |
| thiamin | 0.2 μg | sterilize by filtration |

The plasmid DNA of a DV9 transformant was isolated, designated as pNIC-1.3 and characterized by agarose gel electrophoresis (Sambrook et al.: Molecular Cloning, A Laboratory Manual 1989 Cold Spring Harbor Laboratory Press) and by comparison with standard DNA fragments of a known length. Plasmid pNIC-1.3 contains an insertion with a length of 7 kbp. The complementation capacity of pNIC-1.3 was checked by renewed transformation of the panD mutant DV9. The transformants obtained were again capable of growing in medium E free of β-alanine under the conditions indicated above.

The subcloning of the 7 kb insert took place by cleaving the plasmid pNIC-1.3 with the restriction enzymes BamHI (Pharmacia Biotech (Freiburg, Germany), product description BamHI, code No. 27-0868-03), EcoRI (Pharmacia Biotech (Freiburg, Germany), product description EcoRI, code No. 27-0884-03) and BglII (Pharmacia Biotech (Freiburg, Germany), product description BglII, code No. 27-0946-02) and subsequent ligation into the appropriately restriction-digested vector pK18mob (Schäfer, 1994, Gene, 145:69–73). The ligation batch obtained was electroporated into the *E. coli* panD mutant DV9; the selection for complemented transformants took place as described above and the agar plates contained in this instance 50 μg/ml kanamycin. The plasmids of complemented individual clones were isolated and characterized by means of restriction analyses. An EcoRI subclone, called pNIC-10 in the following, with a DNA insert approximately 3 kb in size was selected for the following sequence analysis.

2. Sequencing of the panD gene

The 3 kb fragment of pNIC-10 was cleaved with various restriction enzymes for its double-stranded sequencing and the fragments subcloned into the plasmids pUC19 or pK18mob. The plasmid DNA used for the sequencing was isolated according to the instructions of the producer with the "QIAGEN Plasmid Mini Kit" (Qiagen, Inc., Chatsworth, Calif., USA) and the determination of the plasmid sizes carried out by agarose gel electrophoresis.

The sequencing took place according to the dideoxy chain-terminating method of Sanger et al. (Proceedings of the National Academy of Sciences USA, 74: 5463–5467, 1977) with modifications according to Zimmermann et al. (Nucleic Acids Research, 18:1067, 1990). The "Cy5-AutoRead Sequencing Kit" of Pharmacia (product NO. 27-2690-02, Freiburg, Germany) was used. The gel electrophoretic separation and analysis of the sequencing reaction took place in a "Long Ranger™ Gel Solution" polyacrylamide gel (FMC BioProducts, Rockland, Me., USA) with the "automatic Laser-Fluorescence (A.L.F.) Express DNA Sequencing Device" of Amersham Pharmacia Biotech (Uppsala, Sweden). The raw sequencing data obtained were subsequently processed using the Staden program packet (Nucleic Acids Research, 14:217–231, 1986) version 97-0. All individual sequences of the pNIC-10 clones were assembled to a cohesive contig 3060 bp in length which was designated as contig13. The computer-supported coding-range analysis with the program XNIP (Staden, 1986, Nucleic Acids Research, 14:217–231) of the entire DNA fragment resulted in the identification of five open reading frames (ORF's).

FIG. 1 shows a restriction map of contig13 as well as the position of the ORF's designated as orf-1 to orf-5. Homology analyses were carried out with the "BLAST search programs" (Gish and States, 1993, Nature of Genetics, 3:266–272; Altschul et al., 1990, Journal of Molecular Biology, 215:403–410), which were made available via the online service of the NCBI server of the "National Library of Medicine" (Bethesda, Md., USA). The analysis of contig13 showed that orf-3 is the panD-gene. Orf-3 is designated in the following as panD. The nucleotide sequence of the DNA fragment carrying the panD gene is shown as SEQ ID NO:1. The amino-acid sequence of the panD gene product resulting with the above methods, namely, L-aspartate 1-decarboxylase, is shown as SEQ ID NO:2.

EXAMPLE 2

Cloning and sequencing of the genes panB and panC from *C. glutamicum*

1. Cloning of the Genes panB and panC

Chromosomal DNA from *C. glutamicum* ATCC13032 was isolated as described in Schwarzer and Pühler (Bio/Technology 9 (1990) 84–87) and cleaved with the restriction endonuclease Sau3A. After gel electrophoretic separation DNA fragments were extracted in a size range of 3 to 7 kb and 9 to 20 kb and subsequently ligated into the singular BamHI cleavage site of vector pBR322. The *E. coli* strain DH5αamcr (Grant et al., Proceedings of the National Academy of Sciences of the United States of America USA, 87 (1990) 4645–4649) was transformed with the ligation batches (Hanahan, Journal of Molecular Biology 166 (1983) 557–580). Insert-carrying colonies were identified using their tetracycline sensitivity after being inoculated onto LB agar plates containing 10 μg/ml tetracycline. 8 groups, each of which contained 400 plasmids with an insert size of 9 to 20 kb, and 9 groups, each of which contained 500 plasmids with an insert size of 3 to 7 kb, were isolated by plasmid preparations (Sambrook et al., Molecular Cloning. A Laboratory Manual (1989) Cold Spring Harbor Laboratory Press) from combined clones. The *E. coli* panB mutant SJ2 (Cronan et al. 1982, Journal of Bacteriology 149:916–922) was transformed with this gene bank by electroporation (Wehrmann et al 1994, Microbiology 140:3349–3356). The transformation batches were plated out directly onto CGXII medium with 15 m/l agar (Keilhauer et al., Journal of Bacteriology (1993) 175:5595–5603). Plasmid DNA was isolated from clones cable of growing without supplementation with pantothenate (Sambrook et al., Molecular Cloning. A Laboratory Manual (1989) Cold Spring Harbor Laboratory Press). The ability to complement the panB defect of the E. coli mutant SJ2 in a heterologous manner was able to be corroborated in the case of 8 plasmids by retransformation.

A restriction mapping was carried out with these 8 plasmids. One of the plasmid vectors investigated, called pUR1 in the following, contained an insert of 9.3 kb (FIG. 2). The transformation of the E. coli panC mutant DV39 (Vallari and Rock 1985, Journal of Bacteriology 164:136-f142) established that the vector pUR1 was likewise able to complement the panC defect of this mutant.

2. Sequencing of the panB and panC Gene

A 2.2 kb fragment of the insert (FIG. 2) of pUR1 was sequenced according to the dideoxy-chain terminating method of Sanger et al (Proceedings of the National Academy of Sciences of the United States of America USA (1977) 74:5463–5467). For this, subclones were produced at first by exonuclease III which subclones were sequenced with the aid of standard primers (universal and reverse primers of the company Boehringer Mannheim, Germany). The gel electrophoretic analysis of the sequence batches took place with the automatic laser fluorescence sequencing device (A.L.F.) of Amersham Pharmacia Biotech (Uppsala, Sweden). The nucleotide sequence obtained was analyzed with the program packet HUSAR (release 4.0, EMBL, Cambridge, GB). The nucleotide sequence is shown as SEQ ID NO:3. Analysis resulted in the identification of two open reading frames. An open reading frame of 813 bp in length, which was identified as panB gene, codes for a polypeptide of 271 amino acids and is shown as SEQ ID NO:4. The second open reading frame, which was identified as panC gene, comprises 837 base pairs. It codes for a polypeptide of 279 amino acids which is shown as SEQ ID NO:5.

EXAMPLE 3

Construction of Vectors for the Expression of panD, panBC and panDBC Genes

The pantothenate biosynthesis genes panD from C. glutamicum and E. coli were amplified using polymerase chain reaction (PCR) as well as synthetic oligonucleotides. The PCR experiments were carried out with the Taq DNA polymerase of the company Gibco-BRL (Eggestein, Germany) in a "PCT-100 Thermocycler" (MJ Research Inc., Watertown Mass., USA). A single denaturing step of 2 minutes at 94° C. was followed by a denaturing step of 90 seconds at 94° C., an annealing step for 90 seconds at a primer-dependent temperature of T=(2AT+4GC)−5° C. (Suggs et al., 1981, pp. 683–693, in: D. D. Brown and C. F. Fox (eds.), Developmental Biology Using Purified Genes, Academic Press, New York, USA) as well as a 90 second extension step at 72° C. The last three steps were repeated cyclically 35 times and the reaction terminated with a final extension step of 10 minutes at 72° C. The products amplified in this manner were ligated, after they had been tested electrophoretically in agarose gel, in accordance with the instructions of the producer into the vector pCR®2.1 (Original TA Cloning Kit, Invitrogene (Leek, Netherlands), product description Original TA Cloning® Kit, cat. No. KNM2030-01).) and subsequently transformed into the E. coli strain TOP10F'. The selection transformants took place by incubation at 37° C. for 24 hours on LB agar plates with 100 μg/ml ampicillin and 40 μg/ml X-Gal (5-bromo-4-chloro-3-indolyl-β-D-galactoside).

Starting from the nucleotide sequences of the pantothenate biosynthesis genes panD (SEQ ID NO:1) and panBC (SEQ ID NO:3) from C. glutamicum ATCC 13032 and from E. coli K12 (W. K. Merkel and B. P. Nichols, 1993, GenBank L17086), PCR primers were synthesized (MWG Biotech, Ebersberg, Germany). These primers were selected in such a manner that the amplified fragments contain the genes as well as their native ribosomal bonding sites but not possible promoter regions. In addition, suitable restriction cleavage sites were inserted which make possible the cloning into the target vector. The sequences of the PCR primers, the inserted cleavage sites (sequence underlined) as well as the amplified gene (fragment size in bp is indicated in brackets) are listed in Table 2.

TABLE 2

| Primer | Sequence with restriction cleavage site | Product | Plasmid |
|---|---|---|---|
| panD-Ec1 | 5'-GAATTCGACAGGGTAGAAAGGTAGA-3' EcoRI (SEQ ID NO: 6) | panD$_{E.c.}$ (462 bp) | pND-D1 |
| panD-Ec2 | 5-AGATCTGGGATAACAATCAAGCAACC-3' BglII (SEQ ID NO: 7) | | |
| panD-Cg1 | 5-CATCTCACGCTATGAATTCT-3' EcoRI (SEQ ID NO: 8) | panD$_{C.g.}$ (405 bp) | pND-D2 |
| panD-Cg2 | 5-ACGAGGCCTGCAGCAATA-3' PstI (SEQ ID NO: 9) | | |
| panBC-E1 | 5'-GGATCCCACAACATCAATTTATCAGG-3' BamHI (SEQ ID NO: 10) | panBC$_{E.c.}$ (1700 bp) | pND-BC1 |
| panBC-E2 | 5'-GGATCCTTAAGTATTACGCCAGCTC-3' BamHI (SEQ ID NO: 11) | | |
| panBC-C1 | 5-GTCGACTCTGAGCTGGTCATCACATC-3' SalI (SEQ ID NO: 12) | panBC$_{C.g.}$ (1700 bp) | pND-BC2 |
| panBC-C2 | 5'-GTCGACACGCAGGGTTGGTACTAGAG-3' SalI (SEQ ID NO: 13) | | |

The E. coli-C. glutamicum shuttle expression vector pZ8-1 (European patent 0.375,889) shown in FIG. 3 was used as base vector for the expression both in C. glutamicum as also in E. coli. The amplified products cloned previously into vector pCR®2.1 were ligated by means of the primer-inserted restriction cleavage sites into the expression vector pZ8-1 treated in the same manner and brought therewith under the control of the tac promoter contained on this plasmid. The sole exception is the product panD$_{E.c.}$. Here the EcoRI-BglII fragment was cloned into the compatible EcoRI-BamHI restriction ends of vector pZ8-1. The particular plasmid designations for the expression plasmids constructed in this manner are indicated in Table 2. The expression vector pZ8-1 with the gene panD$_{E.c.}$ from *E. coli* is named pND-D1 and pZ8-1 with the gene panD$_{C.g.}$ from *C. glutamicum* is named pND-D2. The expression plasmids which contain panBC$_{E.c.}$ and panBC$_{C.g.}$ are designated correspondingly as pND-BC1 and pND-BC2. The cloning strategy for the genes panD$_{E.c.}$ and panD$_{C.g.}$ into vector pZ8-1 is shown by way of example in FIG. 3. The correct cloning of all expression plasmids was checked by sequencing of the particular insert.

Furthermore, an artificial panDBC operon was constructed both with the *E. coli* and also with the *C. glutamicum* panD genes. For the *E. coli* operon the vector pCR2.1 containing panD$_{E.c.}$ was cleaved with EcoRI, the DNA separated in agarose gel and the panD fragment was extracted from the gel, as already described in example 1.1, by the "Nucleotrap Extraction Kit for Nucleic Acids" (Macherey and Nagel, Düren, Germany). The fragment was subsequently ligated into the EcoRI-split plasmid pND-BC1. Plasmids with a correct orientation of the panD gene were obtained in that the ligation mixture was transformed into the panD auxotropic *E. coli* strain DV9 and the latter selected as described in example 1 for complementation of auxotropy. Plasmid DNA of the complemented mutants was isolated and the correct gene arrangement was corroborated by sequencing the insert of the plasmid called pND-DBC 1.

A similar method was used for the construction of the *C. glutamicum* panDBC operon. Vector pCR2.1 containing panD$_{C.g.}$ was split with EcoRI, as a result of which on the one hand the panD$_{C.g.}$ gene was split via the internal primer and on the other hand via an EcoRI cleavage site of the vector. This gene fragment was cloned after being purified into the EcoRI-split vector pZ8-1 and plasmids with the correct panD orientation, called pND-D4, were obtained as described above and checked. Plasmid pND-D4 was subsequently cleared with the restriction enzyme SalI and ligated with the purified panBC fragment, which was obtained by SalI digestion (Pharmacia Biotech (Freiburg, Germany), product description SalI, code No. 27-0882-01) of the plasmid pND-BC2. The electroporation mixture was electroporated into the *E. coli* strain DH5αMCR and the 10 plasmids with the gene arrangement panDBC were determined by restriction analyses. The correct gene arrangement of one of these plasmids designated as pND-DBC2 (FIG. 4) was verified by sequence analysis.

The expression vector pZ8-1 as well as the constructs pND-D1, pND-D2 and pND-DBC1 based on this plasmid were transformed into the *E. coli* strain MG1655 and transformants selected on LB agar (Lennox, 1955, Virology, 1:190)+50 µg/ml kanamycin. The strains obtained were called MG 1655/pZ8-1, MG 1655/pND-D1, MG 1655/pND-D2 and MG1655/pND-DBC1.

The strains ATCC 13032/pZ8-1, ATCC 13032/pND-D 1, ATCC13032/pND-D2 and ATCC13032/pND-DBC2 were obtained by electroporation of the plasmids pZ8-1, pND-D1, pND-D2 and pND-DBC2 into the *C. glutamicum* strain ATCC 13032 and subsequent selection on LB agar (Lennox, 1955, Virology, 1:190)+25 µg/ml kanamycin.

EXAMPLE 4

Formation of Pantothenate by Various *E. coli* K 12 Strains

The quantitative determination of D-pantothenate took place by means of the *Lactobacillus plantarum* pantothenate assay (test strain: *Lactobacillus plantarum* ATCC 8014, cat. No. 3211-30-3; culture medium: Bacto pantothenate assay medium (DIFCO Laboratories, Michigan, USA), cat. No. 0604-15-3). This indicator strain can grow only in the presence of pantothenate in the indicated culture medium and displays a photometrically measurable, linear dependency of the growth on the concentration of pantothenate in the medium. The hemicalcium salt of pantothenate was used for the calibration (Sigma, product designation P 2250). The optical density was determined on an LKB Biochrom Photometer of the company Pharmacia Biotech (Freiburg, Germany) at a measuring wavelength of 580 nm (O.D.$_{.580}$).

For the production of pantothenate of the *E. coli* strains MG 1655/pZ8-1, MG 1655/pND-D 1, MG 1655/pND-D2 and MG1655/pND-DBC1 50 ml test medium (medium E with 50 µg/ml kanamycin) from a culture of the same medium 16 hours old were inoculated with an O.D.$_{.580}$ of 0.1. After 5 and 72 hours incubation of these cultures at 37° C. and 250 rpm the cells were pelletized by a 10-minute centrifugation at 5000×g. The cell-free supernatant obtained was sterilized by filtration and stored until quantification of pantothenate at 4° C.

The quantification of the D-pantothenate in the culture supernatant took place by means of *L. plantarum* ATCC 8014 according to instructions of the manual of the company DIFCO (DIFCO MANUAL, 10$^{th}$ edition, pp. 1100–1102; Michigan, USA). The results of these measurements are shown in Table 3.

TABLE 3

| Strain | Gene | accumulation of OD$_{580}$ and pantothenate (µg/ml) | | | |
|---|---|---|---|---|---|
| | | 5 hrs. | | 72 hrs. | |
| | | OD$_{580}$ | pan. | OD$_{580}$ | pan |
| MG1655/pZ8-1 | — | 2.0 | 0.30 | 2.3 | 1.47 |
| MG1655/pND-D1 | panD$_{E.c.}$ | 2.3 | 0.90 | 2.5 | 6.95 |
| MG1655/pND-DBC1 | panDBC$_{E.c.}$ | 2.0 | 0.96 | 2.0 | 6.96 |
| MG1655/pND-D2 | panD$_{C.g.}$ | 2.2 | 4.07 | 2.3 | 9.66 |

EXAMPLE 5

Formation of Pantothenate by Various Strains of *C. Glutamicum*

The formation of pantothenate by the *C. glutamicum* strains ATCC13032/pZ8-1, ATCC13032/pND-D1, ATCC13032/pND-D2 and *C. glutamicum* ATACC13032/pND-DBC2 was tested in medium CGXII (Keilhauer et al., 1993, Journal of Bacteriology, 175:5595–5603; Table 4) which had been supplemented with 25 µg/ml kanamycin. This medium is designated in the following as *C. glutamicum* test medium. Each 50 ml *C. glutamicum* test medium from a culture of the same medium 16 hours old were inoculated with an O.D.$_{.580}$ of 0.1. After a 48-hour incubation at 30° C. and 150 rpm, the cells were removed by a 10-minute centrifugation at 5000×g, the supernatant sterilized by filtration, and the concentration of pantothenate determined as described in example 4. The results of the production of pantothenate by the various strains of *C. glutamicum* are collated in Table 5.

TABLE 4

| Substance | Amount per liter | Remarks |
|---|---|---|
| $(NH_4)_2SO_4$ | 20 g/l | |
| urea | 5 g/l | |
| $KH_2PO_4$ | 1 g/l | |
| $K_2HPO_4$ | 1 g/l | |
| $MgSO_4 * 7 H_2O$ | 0.25 g/l | |
| MOPS | 42 g/l | |
| $CaCl_2$ | 10 mg/l | |
| $FeSO_4 * 7 H_2O$ | 10 mg/l | |
| $MnSO_4 * H_2O$ | 10 mg/l | |
| $ZnSO_4 * 7 H_2O$ | 1 mg/l | |
| $CuSO_4$ | 0.2 mg/l | |
| $NiCl_2 * 6 H_2O$ | 0.02 mg/l | |
| biotin | 0.5 mg/l | |
| glucose | 40 g/l | autoclave separately |
| protocatechinic acid | 0.03 mg/l | sterilize by filtration |

TABLE 5

| | | Pantothenate (µg/ml) | |
|---|---|---|---|
| Strain | Gene | $OD_{580}$ | pan. |
| ATCC13032/pZ8-1 | — | 21 | 0.19 |
| ATCC13032/pND-D1 | $panD_{E.c.}$ | 20 | 0.32 |
| ATCC13032/pND-D2 | $panD_{C.g.}$ | 19 | 1.78 |
| ATCC13032/pND-DBC2 | $panDBC_{C.g.}$ | 20 | 2.60 |

Figure 1:
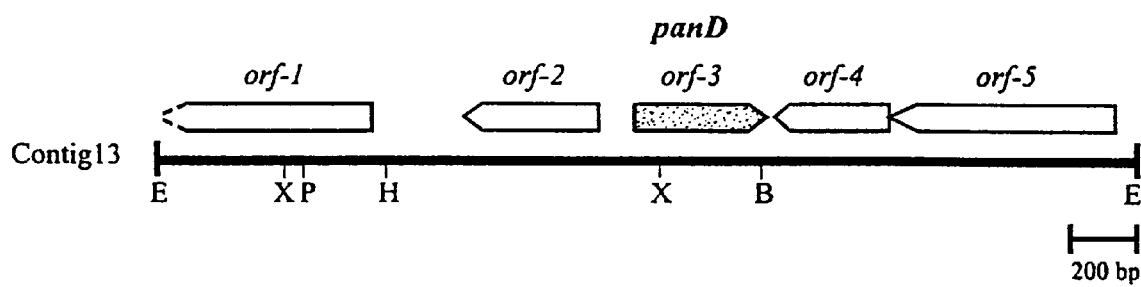
FIG. 1: Map of contig 13 with orf1-orf5
Figure 2:
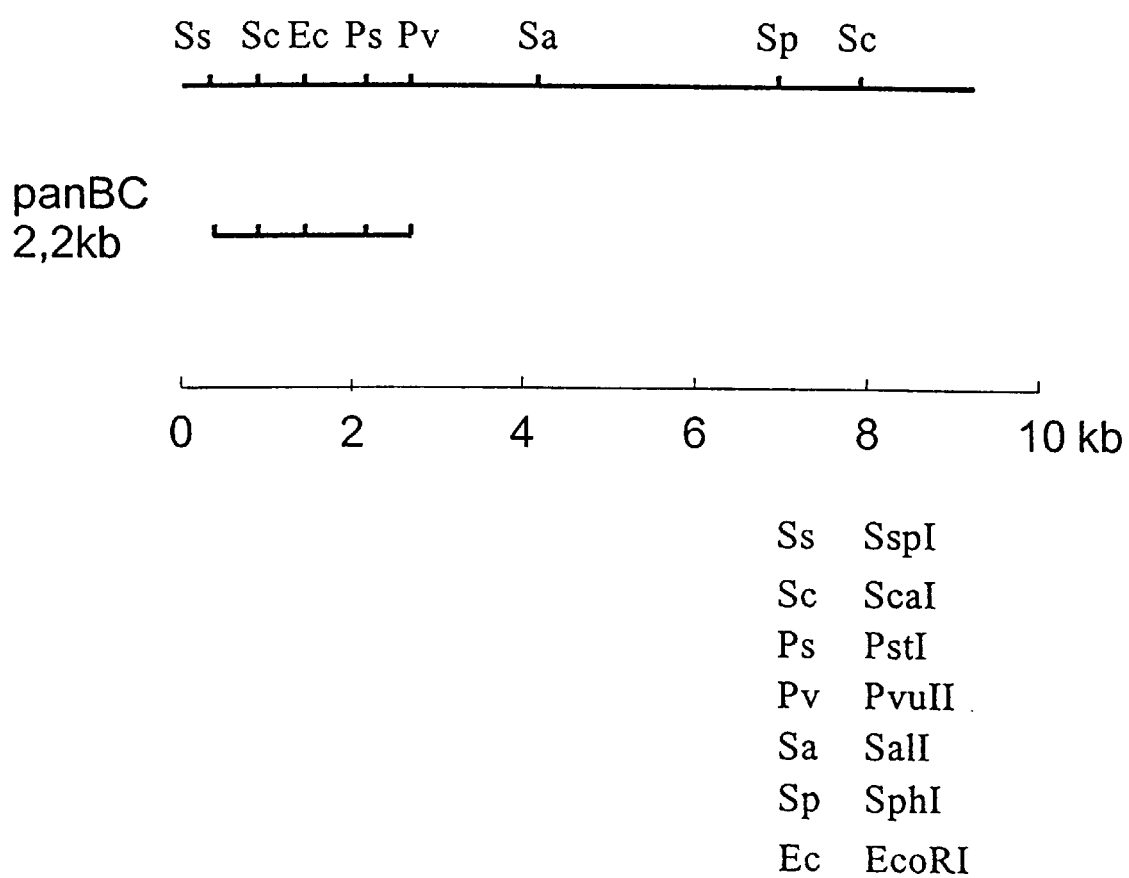
FIG. 2: Map of cloned DNA fragment contained in pUR1 and indication of the position of the sequenced DNA section
Figure 3:
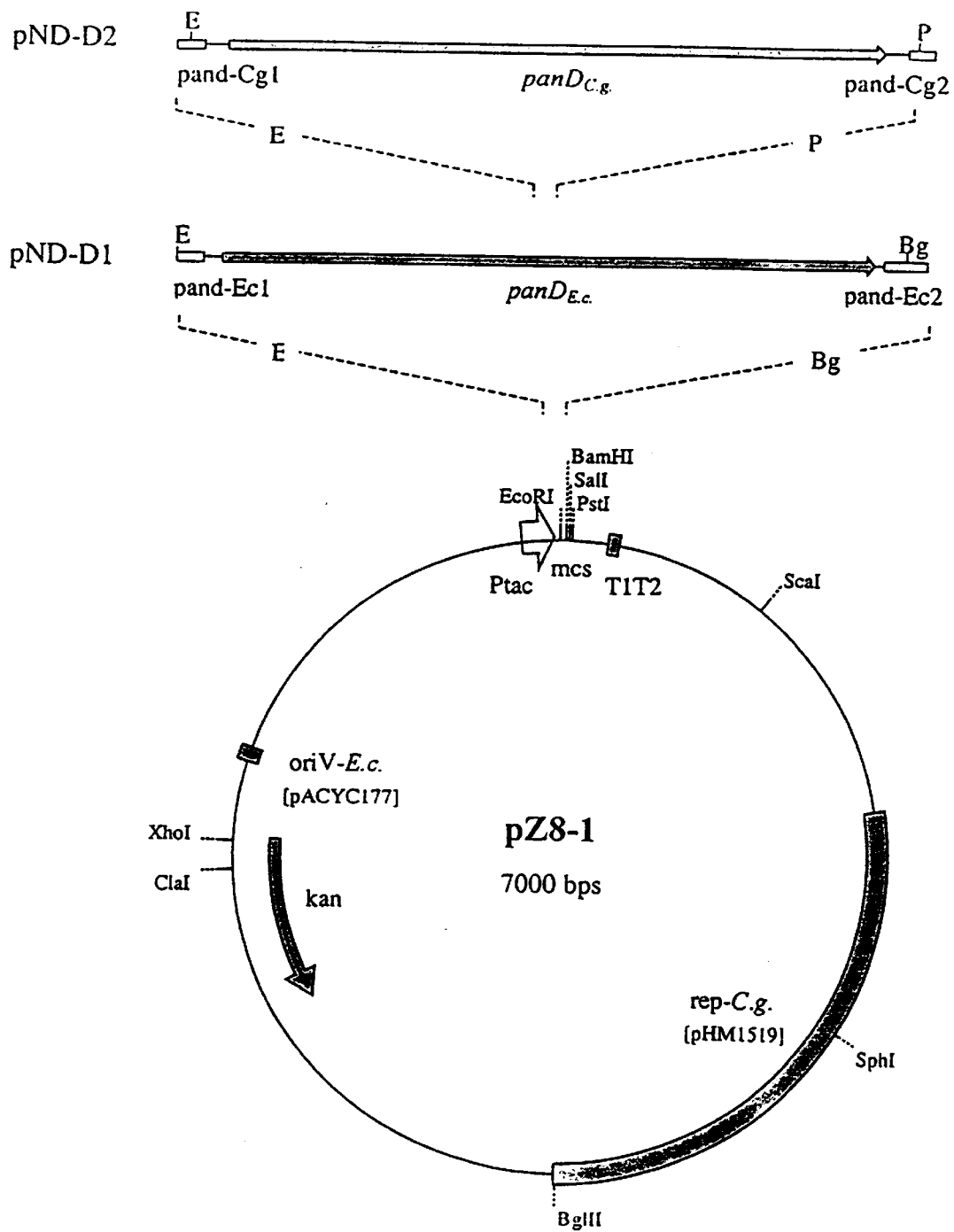
FIG. 3: Map of the plasmids pZ8-1, pND-1 and pND-D2
Figure 4A:
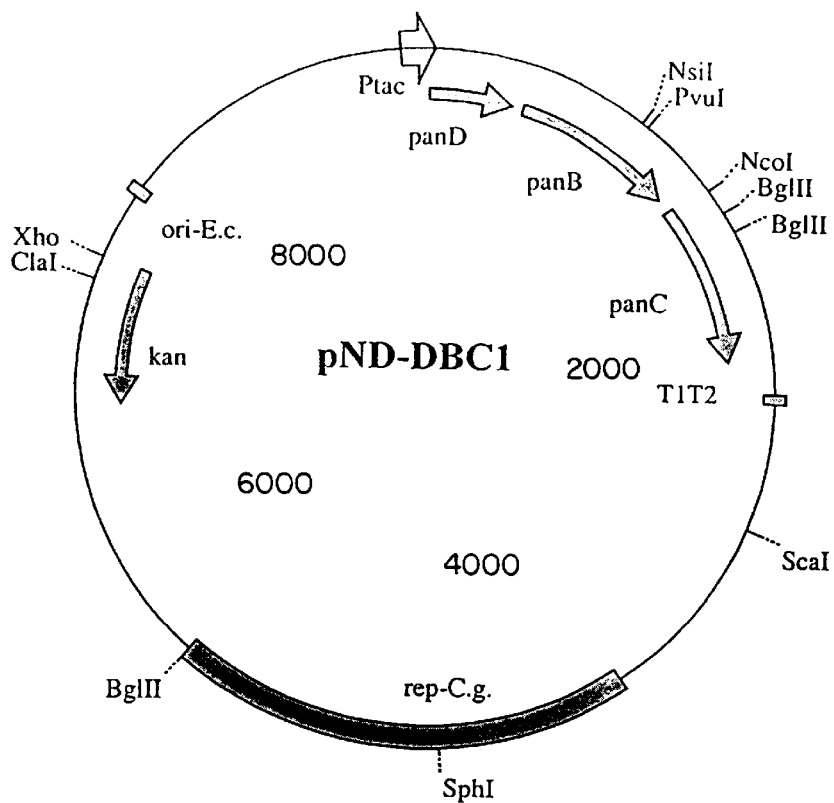
FIG. 4: Map of the plasmids pND-DBC 1 and pND-DBC2
Figure 4B:
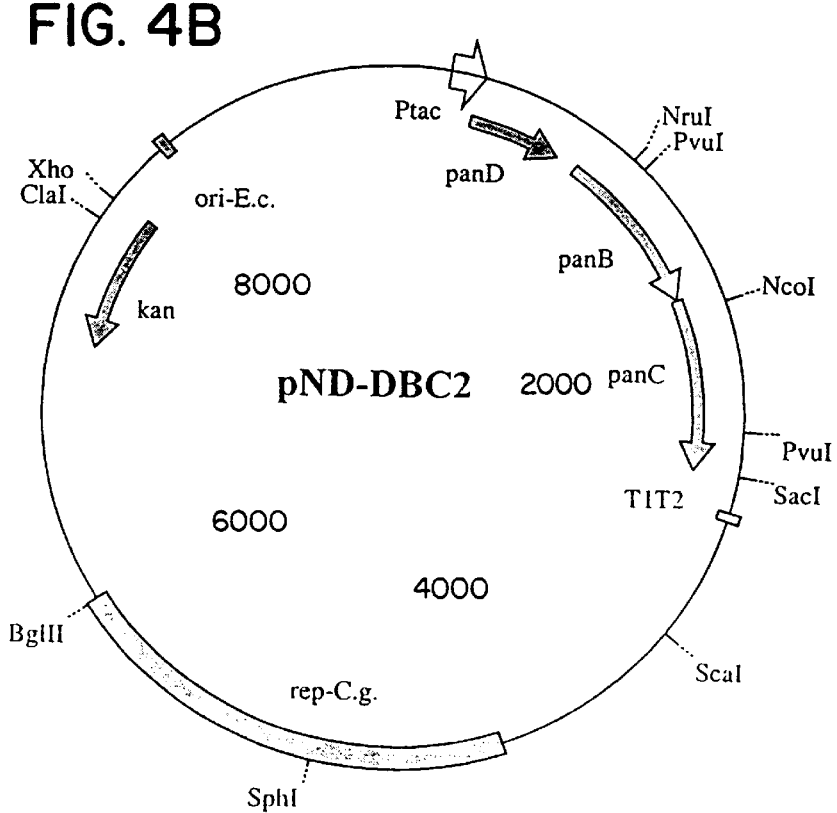

The abbreviations used in the figures have the following significance:

T1T2: Transcription terminator of the rrnB gene

Ptac: tac promoter panB: Coding range of the panB gene panC: Coding range of the panC gene panD: Coding range of the panD gene rep-C.g.: DNA region for replication in *C. glutamicum* oriV-E.c.: Origin for vegetative transfer in *E. coli* kan: Resistance gene for kanamycin pand-Cg1: A primer whose sequence is noted in Table 2.

pand-Cg2: A primer whose sequence is noted in Table 2.

pand-Ec1: A primer whose sequence is noted in Table 2.

pand-Ec2: A primer whose sequence is noted in Table 2.

EcoRI: Cleavage site of the restriction enzyme EcoRI

E: Cleavage site of the restriction enzyme EcoRI

BamHI: Cleavage site of the restriction enzyme BamHI

B: Cleavage site of the restriction enzyme BamHI

BglII: Cleavage site of the restriction enzyme BglII

ClaI: Cleavage site of the restriction enzyme ClaI

H: Cleavage site of the restriction enzyme HindIII

NcoI: Cleavage site of the restriction enzyme NcoI

NruI; Cleavage site of the restriction enzyme NruI

NsiI: Cleavage site of the restriction enzyme NsiI

P: Cleavage site of the restriction enzyme PstI

PstI: Cleavage site of the restriction enzyme PstI

PvuI: Cleavage site of the restriction enzyme PvuI

SacI: Cleavage site of the restriction enzyme SacI

SalI: Cleavage site of the restriction enzyme SalI

ScaI: Cleavage site of the restriction enzyme ScaI

SphI: Cleavage site of the restriction enzyme SphI

X: Cleavage site of the restriction enzyme XbaI

XhoI: Cleavage site of the restriction enzyme XhoI

What is claimed is:

1. An isolated polynucleotide from Corynebacterium comprising a nucleotide sequence encoding the panD gene product, which is aspartate-1-decarboxylase, whose amino acid sequence is set forth in SEQ ID NO: 2.

2. The isolated polynucleotide of claim 1, wherein the nucleotide sequence is set forth in SEQ ID NO: 1, nucleotides 77–484.

3. The isolated polynucleotide of claim 1, wherein the nucleotide sequence is set forth in SEQ ID NO: 1.

4. An isolated polynucleotide from Corynebacterium comprising a nucleotide sequence that hybridizes to the antisense strand of SEQ ID NO: 1 and that encodes aspartate-1-decarboxylase.

5. A vector comprising the isolated polynucleotide of claim 4.

6. The vector of claim 5 that is plasmid vector pND-D2 deposited as *Corynebacterium glutamicum* ATCC 13032/pND-D2 under the designation DGM 12438.

7. The vector of claim 5 that is plasmid vector pND-DBC2 deposited as *Corynebacterium glutamicum* ATCC 13032/pND-DBC2 under the designation DGM 12437.

8. A microorganism comprising the vector of claim 5.

9. The microorganism of claim 8, wherein said microorganism is from the genera selected from the group consisting of Corynebacterium and Escherichia.

10. A method for producing pantothenic acid comprising:
   a) transforming a vector into a microorganism to produce a recombinant microorganism, wherein said vector comprises a panD gene operably linked to a suitable regulatory sequence;
   b) growing said recombinant microorganism under conditions suitable for the production of pantothenic acid in an appropriate culture medium; and
   c) recovering pantothenic acid from said culture medium;
   wherein said panD gene encodes aspartate-1-decarboxylase and originates from Corynebacterium.

11. The method of claim 10, wherein said vector comprising a panD gene is selected from the group consisting of the plasmid vector pND-D2 and the plasmid vector pND-DBC2.

12. The method of claim 10, wherein said transforming results in the introduction of multiple copies of said vector into said microorganism.

13. The method of claim 10, wherein said transforming results in the integration of said panD gene into the chromosome of said microorganism.

14. A method of producing pantothenic acid in Corynebacterium comprising:

a) inserting an expression cassette upstream from the panD gene in said Corynebacterium;
  b) growing said Corynebacterium under conditions suitable for the production of pantothenic acid in an appropriate culture medium; and
  c) recovering pantothenic acid from said culture medium.

15. A method for producing pantothenic acid in Corynebacterium comprising:

a) increasing the stability of the mRNA which is translated from the panD gene in said Corynebacterium; and/or
  b) preventing the degradation of the pcanD gene product in said Corynebacterium, which gene product is aspartate-1-decarboxylase;

wherein said Corynebacterium is grown under conditions suitable for the production of pantothenic acid in an appropriate culture medium, and wherein pantothenic acid is recovered from said culture medium.

16. A method for producing pantothenic acid comprising:

a) transforming a vector into a microorganism to produce a recombinant microorganism, wherein said vector comprises a panD gene, and wherein said vector further comprises a panB gene or a panC gene, which genes are all operably linked to a suitable regulatory sequence;
  b) growing said recombinant microorganism under conditions suitable for the production of pantothenic acid in an appropriate culture medium; and
  c) recovering pantothenic acid from said culture medium; wherein said panD gene encodes aspartate-1-decarboxylase, said panB gene encodes ketopantoate hydroxymethyltransferase and said panC gene encodes pantothenate synthetase and said panD, panB, and panC genes originate from Corynebacterium.

17. The method of claim 16 comprising:

a) transforming a vector into a microorganism to produce a recombinant microorganism, wherein said vector comprises a PanD gene, and wherein said vector further comprises a panB gene and a panC gene, which genes are all operably linked to a suitable regulatory sequence;
  b) growing said recombinant microorganism under conditions suitable for the production of pantothenic acid in an appropriate culture medium; and
  c) recovering pantothenic acid from said culture medium.

18. The method of claim 17, wherein said vector is the plasmid vector pND-DBC2.

19. The method of any one of claims 10, 11, 12, 16, 17, and 18, wherein the expression of the genes on the transformed vector is enhanced by altering the culture medium and/or the conduction of the growth.

20. The method of any one of claims 10, 11, 12, 13, 16, 17, and 18, wherein said microorganism is from the genus Corynebacterium or Escherichia.

21. The method of any one of claims 10 through 18, wherein the culture medium is altered by the addition of a precursor of pantothenic acid selected from the group consisting of aspartate, β-alanine, ketoisovalerate, ketopantoate, or pantoate.

* * * * *